(12) United States Patent
Agate

(10) Patent No.: US 9,297,776 B2
(45) Date of Patent: Mar. 29, 2016

(54) PROBE

(71) Applicant: Aber Instruments Ltd, Aberystwyth (GB)

(72) Inventor: Lindsay Agate, Ceredigion (GB)

(73) Assignee: ABER INSTRUMENTS LIMITED, Aberystwyth (GB)

( * ) Notice: Subject to any disclaimer, the term of this patent is extended or adjusted under 35 U.S.C. 154(b) by 118 days.

(21) Appl. No.: 14/061,681

(22) Filed: Oct. 23, 2013

(65) Prior Publication Data

US 2014/0111224 A1    Apr. 24, 2014

(30) Foreign Application Priority Data

Oct. 24, 2012  (GB) .................................. 1219078.1

(51) Int. Cl.
*G01N 27/22* (2006.01)
*C12M 1/34* (2006.01)

(52) U.S. Cl.
CPC ............. *G01N 27/221* (2013.01); *C12M 41/36* (2013.01); *G01N 27/226* (2013.01)

(58) Field of Classification Search
CPC ............................. G01N 27/07; G01N 27/221
USPC ............ 324/600, 663, 76.11, 754.01, 755.01; 204/672, 673; 600/567
See application file for complete search history.

(56) References Cited

U.S. PATENT DOCUMENTS

2004/0036476 A1    2/2004  Brown
2007/0055173 A1*   3/2007  DeLonzor et al. ............ 600/564
2009/0189618 A1    7/2009  Hoey
2009/0301190 A1    12/2009 Ross, Jr.
2011/0238057 A1*   9/2011  Moss et al. ...................... 606/33

FOREIGN PATENT DOCUMENTS

| GB | 2481832 A | 1/2010 |
|---|---|---|
| GB | 2481832 A | 1/2012 |
| WO | 9011513 A1 | 4/1990 |
| WO | 9011513 A1 | 10/1990 |
| WO | 2010064014 A1 | 6/2010 |
| WO | 2010064014 A1 | 10/2010 |

OTHER PUBLICATIONS

GB Search Report Under Section 17(5) mailed Jan. 16, 2013 for priority application GB 1219078.1.

* cited by examiner

*Primary Examiner* — Vincent Q Nguyen
(74) *Attorney, Agent, or Firm* — Troutman Sanders LLP; Ryan A. Schneider; Benjamin C. Wiles

(57) ABSTRACT

An improved probe designed in particular but not exclusively for measuring the concentration of live biomass. The probe has an insulating body portion arranged to carry a first and second electrode where the probe has a longitudinal axis and the first and second electrodes extend in this longitudinal axis. The body portion has a cross-sectional area perpendicular to the longitudinal axis defined by a major axis and minor axis, wherein the length of the body portion in the major axis is greater than the length of the body portion in the minor axis. The first and second electrodes are positioned on either side of the major axis. This reduces the effect of impedance between the electrode and the liquid through increasing the effective distance between the electrodes.

14 Claims, 3 Drawing Sheets

-- Prior Art --

-- Prior Art --

PROBE

CROSS-REFERENCE TO RELATED APPLICATIONS

This application claims the benefit under 35, U.S.C. §119 (a)-(d) and (f) of GB 1219078.1, filed 24 Oct. 2012, the entire contents and substance of which is hereby incorporated by reference.

BACKGROUND OF THE INVENTION

1. Field of Invention

The present invention relates to an improved probe. The probe has been designed in particular but not exclusively for measuring the concentration of live biomass.

2. Background and Related Art

Capacitance measurement techniques are known for measuring the capacitance (or specific capacitance or dielectric constant) of liquids and suspensions, such as biological cells in ionic aqueous solutions.

Monitoring systems incorporating such measurement capability are beneficial for measuring concentration of live cells. In particular in the brewing industry, the concentration of live yeast can be measured with an on-line capacitance probe. A radio frequency applied from the electrodes of the probe causes ions in the suspending medium (for example wort or green beer) and the cytoplasm of the yeast to move towards the two respective oppositely charged electrodes. As the plasma membrane is non-conducting a buildup of charge results in the cells and are said to be polarized with the yeast cells acting as tiny capacitors within the medium. Non-viable cells or cells with a damaged membrane do not interfere with the signal. Thus, a buildup of charge cannot occur as the ions can freely move across the membrane and so the cells do not become polarized. The measured capacitance is directly proportional to the amount of viable yeast within a sample over a wide concentration range. Such technology can also be utilized for measuring biomass in the field of biotechnology, for example, in controlling cell culture processes.

A variety of different probe arrangements have been utilized. One probe utilizes four electrodes projecting in the longitudinal length of the probe. These four electrodes project into the medium to be measured. The reason that four electrodes are utilized is that the current can be measured between a first pair of electrodes (usually the outermost electrodes) connected to a power input and the other two electrodes (second pair) can be utilized to measure the voltage across them via a high impedance volt meter such that there is virtually no current across this second electrode pair. The voltage typically is not measured across the electrodes through which the current passes due to the significant effect of polarization impedance meaning that the voltage could not be measured accurately. Polarization impedance is the impedance between the electrode and the medium to be measured, which is effectively in series with the impedance of the medium to be measured, thus leading to a distorted and in accurate result for measurement of the medium impedance.

An alternative probe is one where again four electrodes are provided but in this embodiment they are provided such that they do not project into the medium to be measured but instead sit flush against a probe surface and generally extend perpendicular the longitudinal length of the probe. Such a probe is shown in FIG. 1. Referring to FIG. 1, the flange portion 2 seats adjacent an opening in a measurement container such that the electrodes 4 are positioned in the measurement container.

Referring to FIG. 2 an alternative probe arrangement is shown comprising annular electrodes 4 provided within a probe body 6. In this embodiment the probe extends into the measurement chamber. There are advantages associated with the arrangement of FIG. 2 in that the effect of bubbles is reduced. There is still, however, as with the other prior art embodiments described, a problem with respect to polarization between the electrode and the liquid to be measured, which will be measured in series with the measure impedance of the liquid. This is important as the impedance required is the impedance of the liquid without the unwanted influence of the impedance between the electrode and the liquid. In order to reduce this effect the spacing between the electrodes in FIG. 2 is increased which makes the impedance between the electrode and the liquid less significant compared to the impedance of the liquid. Accordingly, the significance of electrode/liquid impedance is reduced, however, there still remains a problem in that the separation of electrodes is determined by the probe size whereby it is desirable to reduce the size of the probe to reduce manufacturing costs and also to reduce the size of the necessary monitoring equipment, thereby enabling a reduced sample size of the testing medium.

A further way of reducing the polarization impedance effect is to use electrode materials such as gold or platinum, however, although this is beneficial the effect of polarization impedance remains.

The present invention provides an improved probe arrangement that is less susceptible to the effect of polarization impedance between the electrodes and the liquid and also enables a significant reduction in probe size.

SUMMARY OF THE INVENTION

Briefly described, in a preferred form, the present invention is a probe having an insulating body portion arranged to carry a first and a second electrode, the probe having a longitudinal axis wherein the first and second electrodes extend in the longitudinal axis, the body portion having a cross-sectional area perpendicular to the longitudinal axis defined by a major axis and a minor axis, wherein the length of the body portion in the major axis is greater than the length of the body portion in the minor axis and wherein the first and second electrodes are positioned on either side of the major axis.

Such an arrangement provides significant advantages over the prior art. A significant advantage of the presently claimed invention is the separation distance between the electrodes thereby reducing the significance of the impedance between the electrode and the liquid. By increasing this distance through the design of the probe body, the overall size of the probe can be reduced as can be the materials for production of the probe. This is particularly important as platinum electrodes are typically used for critical measurements which have also been shown to reduce polarization impedance. However, platinum is extremely expensive and thus reduction in the amount required for use is extremely beneficial, significantly reducing costs whilst also maintaining the functional benefits.

End points beneficially define the length of the body portion in the major axis, wherein the first and second electrodes are positioned such that the current flow path between the first and second electrodes is around an end point of the length of the body portion of the major axis and/or around a distal end of the probe body. As such, even though the first and second electrodes are effectively separated by a small distance through the provision of the body portion of the probe, the body portion of the probe has insulating properties meaning that the current flow path is around an end point of the body portion of the major axis. The effective separation between the first and second electrodes is therefore significantly increased thereby reducing the influence on the measured impedance value through the polarization effect between the current carrying electrodes and the medium under investigation.

The first and second electrodes are beneficially positioned either side of the minor axis. This improves manufacturing capability and also maximizes separation between first and second electrodes. Separation is effectively maximized in this manner by maximizing the current path between the electrodes around the tip of the probe body. By positioning the first and second electrodes on either side of the minor axis, the electrode separation is increased over the probe body tip.

The first and second electrodes beneficially extend generally parallel to the longitudinal axis of the probe. Furthermore, the electrodes are beneficially substantially linear. This provides manufacturing advantages in that no kinks or turns are required in the electrodes. It is of significant benefit to offset the electrodes in this manner as the electrodes can then be in a straight line making it easier to connect them to a PCB in the probe body. Additionally, a lack of kinks or turns in the electrodes means that less material is used. Electrode material is typically extremely expensive when accurate measurement is required meaning that a reduction in material provides significant cost savings.

The probe body beneficially extends to a tip. The electrodes beneficially extend toward but not to the tip. The tip therefore beneficially extends or projects beyond the distal ends of the electrodes. This provides a significant advantage in that the electrodes are protected by the body portion of the probe and also ensure that the separation between the electrodes over the tip of the probe is of sufficient separation.

The body portion preferably at least partially tapers to the tip. The taper is preferably non-uniform. The tapering of the tip may be curved and optionally may extend to a point or may alternatively have a planer end portion.

The first electrode is beneficially arranged to supply a current flow to a medium, and a second electrode is beneficially arranged to receive a current flow from the first electrode via the medium. The first and second electrodes may be termed excitation electrodes. They may be also termed an electrode excitation pair. In use the voltage across the medium may be determined between the first and second electrodes.

The probe beneficially carries a third and fourth electrode. In a preferred embodiment as known in the art and described later herein excitation electrodes are provided together with a sensing pair of electrodes which are used to measure a voltage therebetween.

The third and fourth electrodes are beneficially positioned in either side of the major axis. The third and fourth electrodes are beneficially positioned on either side of the minor axis. The third and fourth electrodes are beneficially positioned such that the separation between the third and fourth electrodes is around an end point of the length of the body portion of the major axis and/or around a distal end of the probe body. The third and fourth electrodes beneficially extend substantially parallel to the first and second electrodes. The first and third electrodes and second and fourth electrodes are beneficially positioned on either side of the major axis. The third and fourth electrodes may be termed sensing electrodes.

The present invention also extends to a biomass measurement apparatus comprising a housing defining a chamber for receipt of a fluid medium and a probe as described herein, the housing configured to position the probe in the chamber.

These and other objects, features and advantages of the present invention will become more apparent upon reading the following specification in conjunction with the accompanying drawing figures.

BRIEF DESCRIPTION OF THE DRAWINGS

Embodiments of the present invention will be now described by way of example only with reference to the accompanying drawings in which.

DETAILED DESCRIPTION OF THE PREFERRED EMBODIMENTS

Figure 1:
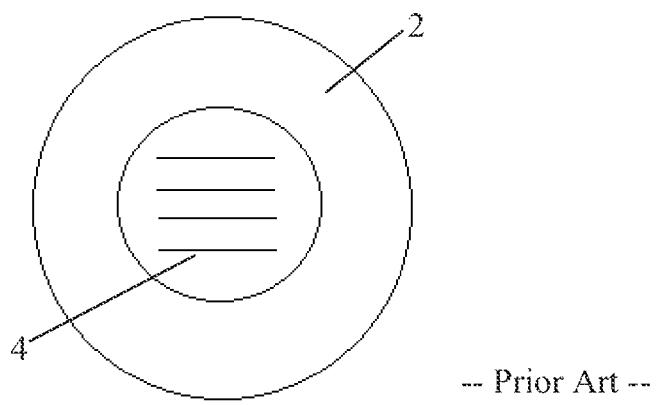
FIG. 1 is a schematic plan view of a probe as known in the art.

To facilitate an understanding of the principles and features of the various embodiments of the invention, various illustrative embodiments are explained below. Although exemplary embodiments of the invention are explained in detail, it is to be understood that other embodiments are contemplated. Accordingly, it is not intended that the invention is limited in its scope to the details of construction and arrangement of components set forth in the following description or illustrated in the drawings. The invention is capable of other embodiments and of being practiced or carried out in various ways. Also, in describing the exemplary embodiments, specific terminology will be resorted to for the sake of clarity.

It must also be noted that, as used in the specification and the appended claims, the singular forms "a," "an" and "the" include plural references unless the context clearly dictates otherwise. For example, reference to a component is intended also to include composition of a plurality of components. References to a composition containing "a" constituent is intended to include other constituents in addition to the one named.

Also, in describing the exemplary embodiments, terminology will be resorted to for the sake of clarity. It is intended that each term contemplates its broadest meaning as understood by those skilled in the art and includes all technical equivalents which operate in a similar manner to accomplish a similar purpose.

Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value.

Similarly, as used herein, "substantially free" of something, or "substantially pure", and like characterizations, can include both being "at least substantially free" of something, or "at least substantially pure", and being "completely free" of something, or "completely pure".

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified. Similarly, it is also to be understood that the mention of one or more components in a composition does not preclude the presence of additional components than those expressly identified.

The materials described as making up the various elements of the invention are intended to be illustrative and not restrictive. Many suitable materials that would perform the same or a similar function as the materials described herein are intended to be embraced within the scope of the invention. Such other materials not described herein can include, but are not limited to, for example, materials that are developed after the time of the development of the invention.

Figure 3:
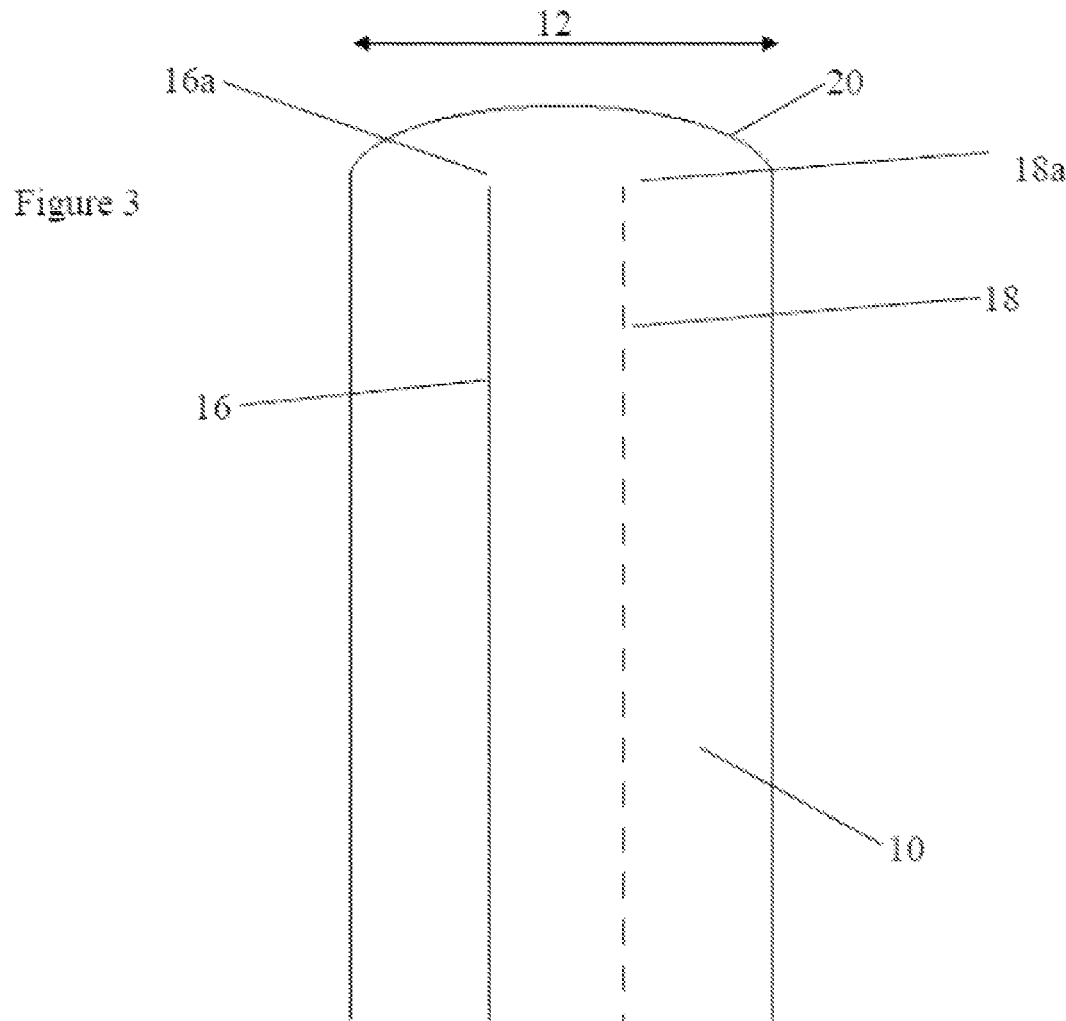
FIG. 3 is a schematic side view of a probe according to an exemplary embodiment of the present invention. It will be appreciated that the opposing side view is a mirror image of the shown side view.

Referring to FIG. 3 there is a probe body (10) having a longitudinal length and being elongate for projection into a medium to be analyzed. The probe has a cross-sectional area perpendicular to the longitudinal axis defined by a major axis and a minor axis wherein the major axis is identified in FIG. 3 by reference numeral (12). The minor axis (14) is identified in FIG. 4 which shows a plan view of the probe. The length of the body portion (10) of the probe in the major axis (12) is greater than the length of the body portion (10) in the minor axis (14), and the length in the major axis is defined between first and second ends (21). A first electrode (16) is shown in FIG. 3. A second electrode (18) is shown in dashed lines indicating that it is provided on the opposite side of the probe body (10) as clearly identified in FIG. 4. Each electrode extends to distal ends 16a, 18a, respectively. The first and second electrodes (16, 18) are spaced apart along the major axis (12). It will be appreciated that the electrodes (16, 18) may be embedded into, adhered to, or otherwise secured to the body (10) such that the body (10) provides protection for the electrodes whilst not significantly reducing their functionality.

The tip (20) of the body portion (10) provided at a distal end of the probe beneficially tapers towards the end. The first and second electrodes (16, 18) are provided such that they do not extend to the end of the tip (20) in order to ensure separation in a direction over the end of the tip (20) is not less than the separation around the probe body (10) between the respective first and second electrodes (16, 18). For this reason to reduce the longitudinal length portion of the tip not carrying the electrodes (16, 18) the electrodes are provided on opposing sides of the minor axis in addition to being provided on opposing sides of the major axis. This also reduces manufacturing costs as the electrodes are in a straight line for connection into a PCB in the probe body.

Figure 4:
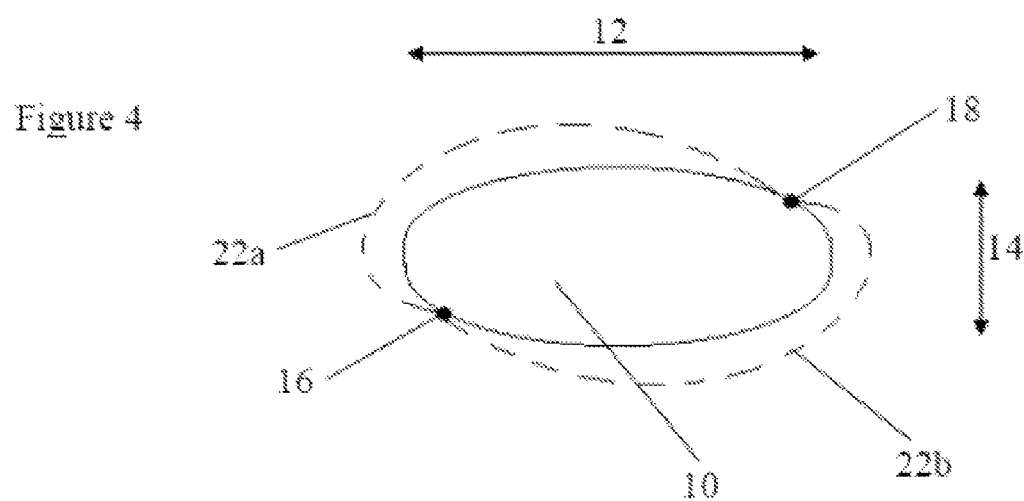
FIG. 4 is a schematic plan view of a probe according to an exemplary embodiment of the present invention.

Referring to FIG. 4, the separation around the probe body (10) is identified by dashed lines (22a, 22b). These lines indicate the separation between the first and second electrodes (16, 18) and identify the route the current must take between the first and second electrodes (16, 18), meaning that the current flow path is around end points defining the major axis. It will also be appreciated as described with respect to FIG. 3 that the current may pass over the tip (20) of the probe body (10), and as such the electrodes do not project to the tip. Instead the electrodes are spaced away from the distal end of the tip (20).

In use the apparatus of FIG. 3 and FIG. 4 utilizes the electrodes (16, 18) to drive current through a sample. A potential drop across the liquid or suspension is detected and the capacitance of the liquid or suspension can be determined using known techniques. Due to the increased separation between the first and second electrodes (16, 18) the measured effect of the electrode polarization in series with the suspension that is under measurement investigation is minimized due to the distance over which the measurement of the liquid or suspension is made.

Figure 5:
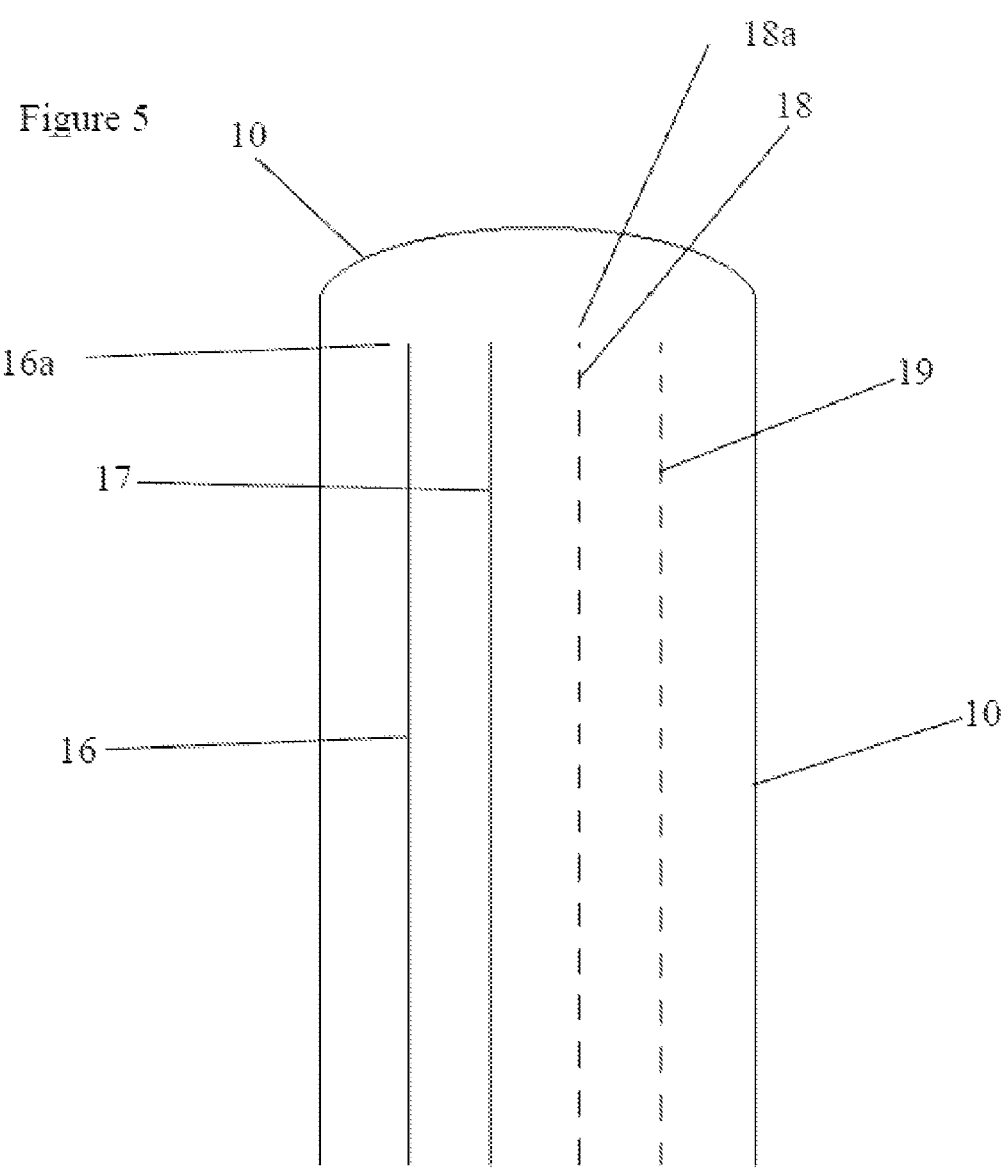
FIG. 5 is a schematic side view of a probe according to an embodiment of the present invention and again it will be appreciated that the opposing side view is a mirror image of the first side view.
Figure 6:
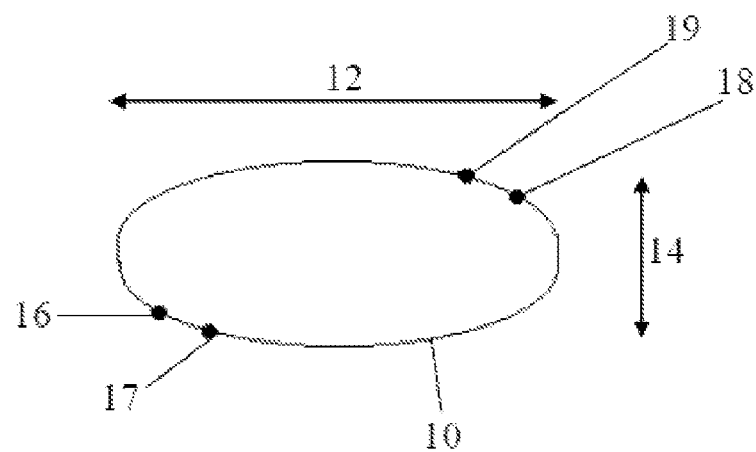
FIG. 6 is a schematic plan view of a probe according to an exemplary embodiment of the present invention as described with respect to FIG. 5.

Referring now to FIGS. 5 and 6, in a preferred embodiment the present invention utilizes a four terminal electrode probe again having a first and second electrodes (16, 18) and third and fourth electrodes (17, 19). A voltage generator is provided in use to generate a sinusoidal excitation voltage (although other excitation waveforms could be employed) and the first and second electrodes (16, 18) are used to drive current through the sample. The third and fourth electrodes (17, 19) are use to detect the potential drop across the sample between the third and fourth electrodes (17, 19). This potential is detected with a high impedance differential amplifier such that there is virtually no current flowing across from electrode (17) to electrode (19) electrode solution interfaces. This is a known way of measuring the capacitance of a medium. A further method of analyzing a test medium is described in GB2481832, which utilizes voltage measurement between both sets of electrodes (16, 18) and (17, 19).

With respect to the preferred embodiment shown in FIGS. 5 and 6, it will be appreciated that the separation between electrodes (16, 18) and electrodes (17, 19) is maximized as a result of the shape of the probe body (10). This has the effect of minimizing the relevance of the polarization impedance between electrodes and the medium to be tested as the significance of this polarization impedance becomes small relative to the amount of the medium to analyze. This improves accuracy of capacitance measurement. In combination with the method disclosed in GB2481832, the capacitance measurement accuracy can be significantly improved.

Figure 2:
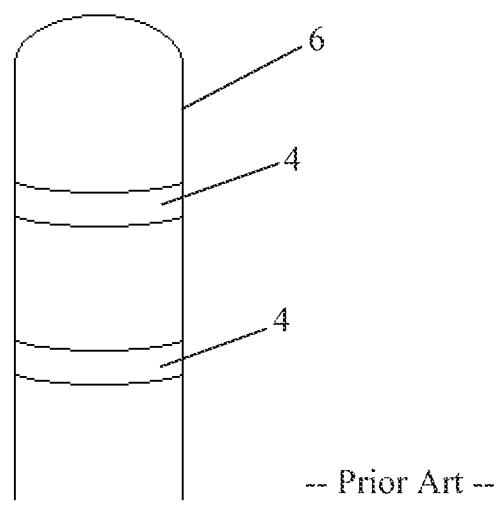
FIG. 2 is a schematic side view of an alternative probe design as known in the art.

As described above, there are significant benefits associated with the accuracy of the capacitance measurements using a probe as described herein. Further significant advantages of the claimed invention relate to manufacturing of the probe. Due to the requirement for certain separation of the electrodes, prior art arrangements such as disclosed in FIGS. 1 and 2 require expensive probe designs having significant size. The present invention enables reduction in the size of the probe thereby reducing the materials required and also reducing the size of the associated measurement system. As described above, the electrodes do not require bending in order to achieve a reduced cross-sectional are of the probe body (10). This reduces manufacturing costs and also reduces the amount of material required, where in the event of high accuracy being required, the electrode material may be platinum or gold. Furthermore, linear electrodes are significantly easier to manufacture than annular electrodes as disclosed, for example, in FIG. 2. The reason for utilizing annular electrode arrangements as described in the art, however, is that they provide reasonable performance due to the separation available when providing annular electrodes. The present invention renders the requirement for annular electrodes unnecessary due to the electrode separation achieved.

Numerous characteristics and advantages have been set forth in the foregoing description, together with details of structure and function. While the invention has been disclosed in several forms, it will be apparent to those skilled in the art that many modifications, additions, and deletions, especially in matters of shape, size, and arrangement of parts, can be made therein without departing from the spirit and scope of the invention and its equivalents as set forth in the following claims. Therefore, other modifications or embodiments as may be suggested by the teachings herein are particularly reserved as they fall within the breadth and scope of the claims here appended.

What is claimed is:

1. A probe having an elongate insulating body portion, the elongate insulating body portion having a longitudinal length extending to a body portion tip, and a first and second electrode extending lengthwise towards, but terminating before, the body portion tip, the first and second electrodes each extending to a first and second distal end, respectively, that terminates before the body portion tip;
   wherein the first and second distal ends are in a fixed location relative to the elongate insulating body portion;
   wherein the elongate insulating body portion has a cross-sectional area perpendicular to the longitudinal axis defined by a major axis and a minor axis;
   wherein the length of the elongate insulating body portion in the major axis is greater than the length of the elongate insulating body portion in the minor axis; and
   wherein the first and second electrodes extending to their respective distal ends are positioned on either side of the major axis.

2. The probe according to claim 1, wherein the length of the elongate insulating body portion in the major axis is defined between first and second ends;
   wherein the first and second electrodes are positioned such that the current flow path between the first and second electrodes is around the first and/or second ends of the elongate insulating body portion of the major axis and/or around the body portion tip.

3. The probe according to claim 1, wherein the first and second electrodes are positioned either side of the minor axis.

4. The probe according to claim 1, wherein the first and second electrodes extend generally parallel to the longitudinal length of the probe.

5. The probe according to claim 1, wherein the electrodes are substantially linear.

6. The probe according to claim 1, wherein the elongate insulating body portion at least partially tapers towards the body portion tip.

7. The probe according to claim 1, wherein the first electrode is arranged to supply a current, and the second electrode is arranged to receive a current.

8. The probe according to claim 1, wherein the probe carries a third and fourth electrode.

9. The probe according to claim 8, wherein the third and fourth electrodes are positioned on either side of the major axis.

10. The probe according to claim 8, wherein the third and fourth electrodes are positioned on either side of the minor axis.

11. The probe according to claim 8, wherein the third and fourth electrodes are positioned such that the separation between the third and fourth electrodes is around an end point of the length of the elongate insulating body portion of the major axis and/or around a distal end of the elongate insulating body portion.

12. The probe according to claim 8, wherein the third and fourth electrodes extend substantially parallel to the first and second electrodes.

13. The probe according to claim 8, wherein the first and third electrode pair and second and fourth electrode pair are positioned on either side of the major axis.

14. A biomass measurement apparatus comprising:
   a housing defining a chamber for receipt of a fluid medium; and
   the probe according to claim 1;
   wherein the housing is configured to position the probe in the chamber.

* * * * *